| United States Patent [19] | [11] 3,990,884 |
|---|---|
| Barker | [45] Nov. 9, 1976 |

[54] HERBICIDAL COMPOSITION COMPRISING 4-CHLORO-2-BUTYNYL m-CHLOROCARBANILATE

[75] Inventor: Christopher Holroyd Barker, Cambridge, England

[73] Assignee: Fisons Limited, United Kingdom

[22] Filed: Sept. 19, 1974

[21] Appl. No.: 507,581

Related U.S. Application Data

[63] Continuation of Ser. No. 159,459, July 2, 1971, abandoned, which is a continuation-in-part of Ser. No. 80,160, Oct. 12, 1970, abandoned.

[30] Foreign Application Priority Data

Oct. 23, 1969 United Kingdom............... 51973/69

[52] U.S. Cl. ............................. 71/111; 71/DIG. 1
[51] Int. Cl.² ......................................... A01N 9/20
[58] Field of Search.................... 71/111, DIG. 1

[56] References Cited
UNITED STATES PATENTS

| 2,906,614 | 9/1959 | Hopkins et al...................... 71/111 |
|---|---|---|
| 3,235,363 | 2/1966 | Luckenbaugh ........................ 71/92 |
| 3,385,692 | 5/1968 | Knowles............................ 71/111 X |
| 3,674,459 | 6/1972 | Alt..................................... 71/100 |
| 3,690,863 | 9/1972 | Gerike................................ 71/100 |

FOREIGN PATENTS OR APPLICATIONS

| 815,510 | 2/1957 | United Kingdom.............. 71/DIG. 1 |
|---|---|---|

*Primary Examiner*—Joseph Paul Brust
*Attorney, Agent, or Firm*—Wenderoth, Lind, & Ponack

[57] ABSTRACT

An improved 4-chloro-2-butynyl m-chlorocarbanilate herbicidal composition comprises:
a. 10 to 30% 4-chloro-2-butynyl m-chlorocarbanilate;
b. 10 to 30% condensate of a fatty alcohol containing from 8 to 16 carbon atoms with from 2 to 6 moles of ethylene oxide;
c. 5 to 15% emulsifier other than the condensate; and
d. 25 to 75% hydrocarbon oil;

by weight based on the total weight of these 4 specified ingredients.

19 Claims, No Drawings

HERBICIDAL COMPOSITION COMPRISING 4-CHLORO-2-BUTYNYL M-CHLOROCARBANILATE

CROSS REFERENCE TO RELATED APPLICATION

This is a continuation of application Ser. No. 159,459, filed July 2, 1971, now abandoned which application is a continuation-in-part of Ser. No. 80,160, filed Oct. 12, 1970, now abandoned.

The present invention relates to herbicidal compositions and their use.

No matter how useful a herbicide is, it is desirable that as small a weight as possible of it be employed to obtain a given effect, so as to minimise any problems, e.g. as to pollution, to which its residue could give rise after the herbicide has performed its desired function.

4-chloro-2-butynyl m-chlorocarbanilate is a known herbicide and is normally formulated as a solution in a hydrocarbon oil containing an emulsifier. In use, the formulation is conventionally applied after dilution with water. It has now surprisingly been discovered that replacing 10–30% of the hydrocarbon by a particular condensate produces a composition which not only may contain a higher maximum concentration of 4-chloro-2-butynyl m-chlorocarbanilate than the 12.5% by weight maximum possible in the conventional formulation but which moreover in use results in a given level of weed control when less 4-chloro-2-butynyl m-chlorocarbanilate is applied per unit area than when the initial formulation is used. Hence, any possible residue problems can be reduced, or greater activity can be achieved for a given level of herbicide application.

Accordingly, the present invention is for a herbicidal composition comprising:

a. 10 to 30% 4-chloro-2-butynyl m-chlorocabanilate;
b. 10 to 30% condensate of a fatty alcohol containing from 8 to 16 carbon atoms with from 2 to 6 moles of ethylene oxide;
c. 5 to 15% emulsifier other than the condensate; and
d. 25 to 75% hydrocarbon oil;

by weight based on the total weight of these 4 specified ingredients.

Preferably, the composition contains 15–30% and more preferably 20-30% by weight of the 4-chloro-2-butynyl m-chlorocarbanilate, based on the total weight of the 4 specified ingredients.

The nature of the emulsifier (c) is not critical, and non-ionic, cationic and anionic emulsifiers may be used, as well as mixtures thereof. Suitably the composition contains 7.5 to 12.5% by weight of the emulsifier, based on the total weight of the 4 specified ingredients.

The fatty alcohol/ethylene oxide condensate (b) suitably forms from 15 to 25% by weight of the composition, based on the total weight of the 4 specified ingredients. The fatty alcohol (i.e. primary alcohol, usually straight chain) of 8 to 16 carbon atoms may comprise 1-dodecanol (e.g. lauryl alcohol) and may be condensed with 4 moles of ethylene oxide (per mole of fatty alcohol).

The hydrocarbon oil (d) usually comprises an aromatic hydrocarbon. Any of the usual hydrocarbon oils may be used as the solvent, e.g. xylene (which may be mixed with kerosene). An aromatic hydrocarbon fraction of boiling range 165°–200° C is preferred however. Kerosene is the hydrocarbon mixture of boiling range 150°–300° C obtained by the distillation of petroleum or shale oil.

The composition may contain other additives such as dyes and stabilisers, suitably in amounts up to 1% by weight of the formulation. Generally it consists substantially of the 4 ingredients (a), (b), (c) and (d), e.g. with such dyes or stabilisers.

The present composition can be formed merely by mixing the ingredients.

In use, the composition, e.g. an emulsifiable concentrate consisting substantially of the ingredients (a), (b), (c) and (d), is suitably dispersed in water to form an emulsion. The degree of dilution does not appear to be critical but, in general, for spraying from the earth a concentration of 1 lb total weight of ingredients (a), (b), (c) and (d) in 10 to 100 gallons (1 kg in 100 to 1,000 liters) of water, and for spraying from aircraft 1 lb total weight of the 4 ingredients in 2 to 10 gallons (1 kg in 20 to 100 liters) of water is used, so that an overall general range is 1 lb total weight of the 4 ingredients in 2 to 100 gallons (1 kg in 20 to 1,000 liters) of water. Gallons in this specification are Imperial gallons.

The composition may also contain other active ingredients such as herbicides and insecticides.

The present invention is also for a method of combating weeds at a locus infested or liable to be infested with them, which method comprises applying to the locus a weed-combating amount of the composition. The method is particularly useful where sugar beet or a cereal crop, such as wheat or barley, is growing or is to grow at the locus. The composition combats wild oats (*Avena fatua*) among such plants.

The rate of application of the composition may be, for example, 0.05 to 2.0 lbs per acre (0.06 to 2.2 kg per hectare) based on the content of 4-chloro-2-butyl m-chlorocarbanilate in the composition.

The following Examples are given to illustrate the invention. The lauryl alcohol referred to is that obtained from coconut oil and consisting predominantly of 1-dodecanol.

EXAMPLE 1

A suitable emulsifiable oil formulation consists of the following weight proportions of ingredients:

| | |
|---|---|
| 4-chloro-2-butynyl m-chlorobanilate | 25% |
| emulsifier CA/T 300 (mixture of calcium dodecylbenzenesulphonate and condensate of tributylphenol with 30 moles of ethylene oxide) | 12% |
| condensate of lauryl alcohol with 4 moles of ethylene oxide | 24% |
| mixture of xylene and kerosene (1:1 by volume) | 39% |

EXAMPLE 2

An emulsifiable oil formulation (Composition A) was prepared from the following weight proportions of ingredients:

| | |
|---|---|
| 4-chloro-2-butynyl m-chlorocarbanilate | 25% |
| emulsifier (mixture of anionic and nonionic emulsifiers) | 12% |
| condensate of lauryl alcohol with 4 moles of ethylene oxide | 24% |
| mixture of xylene + kerosene (1:1 by volume) | 39% |

For comparison, a standard formulation (Composition B) was prepared from the following weight proportions of ingredients:

| | |
|---|---|
| 4-chloro-2-butynyl m-chlorocarbanilate | 12.5% |
| emulsifier (same mixture of anionic and nonionic emulsifiers as in Composition A) | 10% |
| mixture of xylene + kerosene (1:1 by volume) | 77.5% |

EXAMPLE 3

The two compositions of Example 2 were diluted with water and sprayed onto plots of barley infested with wild oats at a time when the majority of the weeds had between 1 and 2½ leaves. The rates of dilution were adjusted so as to give a spray of 3.5 ounces (100g) (Composition A) and 5 ounces (140 g) (Composition A and B) of active ingredient in 20 gallons (90 liters) of spray liquid per acre (0.4 hectare).

The percentage control of weeds, based on the mean of 56 sites treated in various countries, under differing conditions of soil and climate, there being several (e.g. 6) replications at each site, was as follows:

| | | |
|---|---|---|
| Composition A | 5 ounces/acre (350 grammes/hectare) | 82.3% |
| Composition B | 5 ounces/acre (350 grammes/hectare) | 74.4% |
| Composition A | 3.5 ounces/acre (245 grammes/hectare) | 77.5% |

It can be seen from this very great number of experiments that when the same amount of active ingredient is applied, the present composition is significantly more active, killing over a quarter of the weeds left unaffected by the comparative composition.

It can also be seen that the present composition achieves better weed control than the comparative composition even when less than three-quarters of the amount of 4-chloro-2-butynyl m-chlorocarbanilate is applied.

The present composition also showed significantly greater reliability than the comparative composition, in these experiments.

This is illustrated by the Table below which records the percentage of the experiments using an application rate of 5 ounces per acre (350 grammes per hectare) achieving given levels of control over weeds.

| Control | Composition A | Composition B |
|---|---|---|
| Over 60% | 93% | 79% |
| Over 70% | 80% | 72% |
| Over 80% | 61% | 54% |
| Over 90% | 41% | 14% |

EXAMPLE 4

A suitable emulsifiable oil formulation consists of the following ingredients:

| | |
|---|---|
| 4-chloro-2-butynyl m-chlorocarbanilate, technical (88% by weight pure) | 28.4% weight/volume |
| Texofor B4 (lauryl alcohol condensed with 4 moles of ethylene oxide) | 24.0% weight/volume |
| Arylan CA (calcium dodecyl benzene sulphonate, 70% solution) | 8.4% weight/volume |
| Sapogenat T-500 (tributylphenol condensed with 50 moles of ethylene oxide) | 3.6% weight/volume |
| Waxoline Red OS (an oil-soluble red dye) | 0.2% weight/volume |
| Xylene | 44% volume/volume |

EXAMPLE 5

A suitable emulsifiable oil formulation consists of the following ingredients:

| | |
|---|---|
| 4-chloro-2-butynyl m-chlorocarbanilate, technical (88% by weight pure) | 28.4% weight/volume |
| Brij 30 (lauryl alcohol condensed with 4 moles of ethylene oxide) | 24.0% weight/volume |
| Arylan CA (calcium dodecyl benzene sulphonates; 70% solution) | 7.2% weight/volume |
| Sapogenat T-500 (tributylphenol condensed with 50 moles of ethylene oxide) | 4.8% weight/volume |
| Waxoline Red OS (an oil-soluble red dye) | 0.2% weight/volume |
| Naphtha 21/99 (an aromatic hydrocarbon fraction of boiling range 165–200° C) | 44% volume/volume |

EXAMPLE 6

The formulation of Example 5 was sprayed at the rate of 5 ounces (140 g) of 4-chloro-2-butynyl m-chlorocarbanilate in 20 gallons (90 liters) of spray liquid per acre (0.4 hectare) on to plots of spring barley infested with wild oats (*Avena fatua*). The treatment was carried out in early May, when the majority of the wild oats had between 1 and 2½ leaves. 48 differing sites were treated, with four replications at each site. For comparison, plots at the same sites were treated with a standard formulation of 4-chloro-2-butynyl m-chlorocarbanilate (Composition B of Example 2) at the same rate.

After ten weeks, the sites were assessed for weed control by comparison with unsprayed control plots. It was found that the plots sprayed with the composition according to the invention had 20.2% of the wild oats in the control plots whereas the plots sprayed with the standard formulation had 27% of the wild oats in the control plots. Hence, the composition according to the invention killed a quarter of the weeds left unaffected by the comparative composition. No damage was observed to the barley crop. These results are the mean of all 48 trials.

EXAMPLE 7

The formulation of Example 5 was sprayed at the rate of 10 ounces (280 g) of 4-chloro-2-butynyl m-chlorocarbanilate in 20 gallons (90 liters) of spray liquid per acre (0.4 hectare) on to plots of sugar beet infested with wild oats (*Avena fatua*). The treatment was carried out in early May, when the majority of the wild oats had between 1 and 2½ leaves. Four differing sites were treated, with four replications at each site. For comparison, plots at the same sites were treated with a standard formulation of 4-chloro-2-butynyl m-chlorocarbanilate (Composition B of Example 2) at the same rate.

After 4 weeks, the sites were assessed for weed control by comparison with unsprayed control plots. It was found that the plots sprayed with the composition according to the invention had 13% of the wild oats in the control plots, whereas the plots sprayed with the standard composition had 30% of the wild oats in the control plots. Hence, the composition according to the invention killed over half the weeds left unaffected by the comparative composition. No damage was observed to the sugar beet crop. These results are the mean of all four trials.

I claim:

1. A herbicidal composition comprising:
   a. 10 to 30% 4-chloro-2-butynyl m-chlorocarbanilate;
   b. 10 to 30% condensate of a fatty alcohol containing from 8 to 16 carbon atoms with from 2 to 6 moles of ethylene oxide;
   c. 5 to 15% emulsifier other than the condensate; and
   d. 25 to 75% hydrocarbon oil;

by weight based on the total weight of these 4 specified ingredients.

2. A composition according to claim 1, containing 15–30% by weight 4-chloro-2-butynyl m-chlorocarbanilate, based on the total weight of the 4 specified ingredients.

3. A composition according to claim 1, containing 20–30% by weight 4-chloro-2-butynyl m-chlorocarbanilate, based on the total weight of the 4 specified ingredients.

4. A composition according to claim 1, wherein the hydrocarbon oil comprises an aromatic hydrocarbon.

5. A composition according to claim 1, wherein the hydrocarbon oil comprises xylene.

6. A composition according to claim 1, wherein the hydrocarbon oil comprises an aromatic hydrocarbon fraction of boiling range 165°–200° C.

7. A composition according to claim 1, containing 15–25% by weight of the condensate, based on the total weight of the 4 specified ingredients.

8. A composition according to claim 1, wherein the condensate comprises a condensate of 1-dodecanol with the ethylene oxide.

9. A composition according to claim 1, wherein the condensate is of the fatty alcohol with 4 moles of ethylene oxide.

10. A composition according to claim 1, which consists substantially of the 4 specified ingredients.

11. A composition according to claim 1, which contains a further herbicide or an insecticide.

12. A composition according to claim 1, which contains water.

13. A composition according to claim 1, which contains water and 1 kg of total weight of ingredients (a), (b), (c) and (d) per 20 to 1000 liters of water.

14. A method of combating weeds at a locus infested or liable to be infested with them, which method comprises applying thereto a weed-combating amount of a herbicidal composition comprising:
   a. 10 to 30% 4-chloro-2-butynyl m-chlorocarbanilate;
   b. 10 to 30% condensate of a fatty alcohol containing from 8 to 16 carbon atoms with from 2 to 6 moles of ethylene oxide;
   c. 5 to 15% emulsifier other than the condensate; and
   d. 25 to 75% hydrocarbon oil;

by weight based on the total weight of these 4 specified ingredients.

15. A method according to claim 14, wherein the composition comprises water and 1 kg of total weight of ingredients (a), (b), (c) and (d) per 20 to 1000 liters of water.

16. A method according to claim 14, wherein a cereal crop is growing or is to grow at the locus.

17. A method according to claim 14, wherein wheat or barley is growing or is to grow at the locus.

18. A method according to claim 14, wherein sugar beet is growing or is to grow at the locus.

19. A method according to claim 14, wherein 0.06 to 2.2 kg of the composition, based on the content of 4-chloro-2-butynyl m-chlorocarbanilate, is applied per hectare.

* * * * *